United States Patent
Werner et al.

(10) Patent No.: US 7,658,091 B2
(45) Date of Patent: Feb. 9, 2010

(54) METHOD FOR THE AUDIBLE OUTPUT OF A PIECE OF INFORMATION IN AN ANALYSIS SYSTEM

(75) Inventors: Karl Werner, Wiesloch (DE); Gertrud Albrecht, Mannheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 204 days.

(21) Appl. No.: 11/565,149

(22) Filed: Nov. 30, 2006

(65) Prior Publication Data
US 2007/0144235 A1   Jun. 28, 2007

(30) Foreign Application Priority Data
Dec. 5, 2005   (EP) ................... 05026525

(51) Int. Cl.
*G01M 1/14* (2006.01)
(52) U.S. Cl. ........................................ 73/1.82
(58) Field of Classification Search .............. 73/1.82, 73/591; 359/22
See application file for complete search history.

(56) References Cited

U.S. PATENT DOCUMENTS

| | | | |
|---|---|---|---|
| 4,014,016 A | 3/1977 | Sherritt et al. ............... 340/21 |
| 6,644,120 B1* | 11/2003 | Braun et al. ................. 73/585 |
| 2003/0114836 A1 | 6/2003 | Estes et al. .............. 604/890.1 |
| 2003/0144582 A1* | 7/2003 | Cohen et al. ............... 600/316 |
| 2004/0037428 A1* | 2/2004 | Keller ......................... 381/60 |
| 2004/0106859 A1 | 6/2004 | Say et al. .................... 600/345 |
| 2004/0167464 A1 | 8/2004 | Ireland et al. ................ 604/66 |
| 2005/0023137 A1* | 2/2005 | Bhullar et al. ............. 204/403.1 |
| 2007/0060869 A1 | 3/2007 | Tolle et al. ................... 604/65 |
| 2007/0060870 A1 | 3/2007 | Tolle et al. ................... 604/65 |

FOREIGN PATENT DOCUMENTS

| | | |
|---|---|---|
| DE | 2550614 | 11/1975 |
| EP | 1256798 | 11/2002 |
| EP | 1498719 | 1/2005 |
| EP | 1759726 A2 | 3/2007 |
| JP | 04001570 | 4/1992 |
| WO | WO99/29429 | 6/1999 |
| WO | WO02/062212 | 8/2002 |
| WO | WO03/039362 | 5/2003 |

OTHER PUBLICATIONS

European Search Report dated Mar. 14, 2006 for EP05026525.

* cited by examiner

*Primary Examiner*—Hezron Williams
*Assistant Examiner*—Tamiko D Bellamy
(74) *Attorney, Agent, or Firm*—Barnes & Thornburg LLP

(57) ABSTRACT

A system for analysing a fluid sample arranged on a test element comprises a data processing unit configured to process results of an analysis of the fluid sample arranged on the test element, an audible signal generator, and a control unit. The control unit may control the audible signal generator to generate an audible test signal that is configured to test the operability of the signal generator to audibly encode information. The audible test signal may include audible features that allow for identification of any deviation of the generated audible test signal from a correctly generated audible test signal, and/or from which malfunction of the signal generator can be detected.

18 Claims, 1 Drawing Sheet

METHOD FOR THE AUDIBLE OUTPUT OF A PIECE OF INFORMATION IN AN ANALYSIS SYSTEM

CROSS-REFERENCE TO RELATED APPLICATIONS

This application is a U.S. counterpart application of, and claims priority to, European Application Serial No. EP 05026525.5 filed Dec. 5, 2005, the disclosure of which is incorporated herein by reference.

FIELD OF THE INVENTION

The invention relates to a method for the audible output of a piece of information by an audible signal generator, where the signal generator is arranged in an analysis system for analysing a sample using a test element, and relates to an analysis system having an audible signal generator.

BACKGROUND

To analyse samples, for example body fluids such as blood or urine, analysis systems are frequently used in which the samples to be analysed are placed on a test element and possibly react with one or more reagents in a test array on the test element before they are analysed. Optical, particularly photometric, and electrochemical evaluation of test elements are the most common methods for quickly determining the concentration of analytes in samples. Photometric and electrochemical evaluations are generally used in the field of chemical analysis, environmental analysis and in particular in the field of medical diagnosis. Especially in the field of blood glucose diagnosis from capillary blood, test elements which are evaluated photometrically or electrochemically carry a great weight.

In recent years, portable meters for determining blood sugar have become significant. They allow an easy-to-use meter, a piercing aid optimized for piercing pain and a single-use test element to be used at any time to determine blood sugar measured values and hence to effect more accurate insulin dosage for the patient in order to stabilize his blood sugar value.

There are various forms of test elements. By way of example, essentially square lamellae, also called slides, are known, in the centre of which there is a multilayer test array. Diagnostic test elements in strip form are called test strips. For the purpose of three-dimensional separation of a detection zone and a sample application point on a test element, capillary test elements are known from the prior art, e.g. from WO 99/29429.

Sample analysis performed using a test element in an analysis system produces an analysis result, e.g. an ascertained blood sugar concentration value. This analysis result is usually indicated on a visual display panel in the analysis system, e.g. on a liquid crystal display. For users who suffer from visual impairment or blindness, an audible output is additionally provided.

WO 03/039362 A1 relates to a reagentless whole-blood glucose meter in which a processor communicates measured concentration results and/or other information to a controller. The controller operates a visual display panel for presenting the information to a user. In addition or as an alternative to the visual display panel, an audible output for the information may be provided.

WO 02/062212 A1 relates to a management system for personal health which comprises an output apparatus which communicates a treatment recommendation to a patient. The output apparatus can transmit the treatment recommendation using audible, visible or tactile means, for example using a warning tone generator or a system indicator.

A piece of information is audibly output usually using an audible signal generator or a loudspeaker.

U.S. Pat. No. 4,014,016 relates to an output system for blind people in which information is transmitted by audible signals. This is an output system in a pocket calculator, for example, in which the digits of a calculation result are output using uniformly spaced tone sequences with a different number of tones at the same frequency.

DE 25 50 614 relates to a method for audible output through the production of an encoded electrical output signal which denotes a recoverable piece of information. This encoded electrical output signal is used to produce a predetermined number of audible tones at essentially the same frequency, the number of these tones denoting the recoverable piece of information. The recoverable piece of information may be at least one decimal number, for example, with the number of audible tones being equal to the decimal number.

SUMMARY

Audible output in an analysis system for analysing a sample using a test element needs to meet particular demands on the operability thereof. The health or even the life of the user may depend on the result of the analysis being output correctly in audible form. By way of example, a measured blood glucose value governs the insulin dose which is administered to a diabetic.

It is therefore desirable to avoid incorrect audible outputs by an audible signal generator in an analysis system for analysing a sample using a test element or to allow them to be identified by the user.

The invention achieves this by a method for the audible output of a piece of information by an audible signal generator, where the signal generator is arranged in an analysis system and the analysis system analyses a fluid sample using a test element, where analysis results are generated and are processed by a data processing unit, and where a control unit in the analysis system actuates the signal generator, so that the signal generator audibly outputs a piece of information, the signal generator sending an audible test signal in order to test the operability of the signal generator.

The invention also relates to an analysis system for analysing a fluid sample using a test element, containing an audible signal generator for audibly outputting a piece of information, an analysing for generating analysis results, a data processing unit for processing the analysis results and a control unit, the control unit being designed such that it actuates the signal generator to send an audible test signal in order to test the operability of the signal generator.

The invention also relates to the use of an audible signal generator, which, for the purpose of audibly outputting a piece of information, is arranged in an analysis system for analysing a sample using a test element, for checking the operability of the signal generator by sending an audible test signal.

DESCRIPTION OF THE ILLUSTRATIVE DRAWINGS

Figure 1:
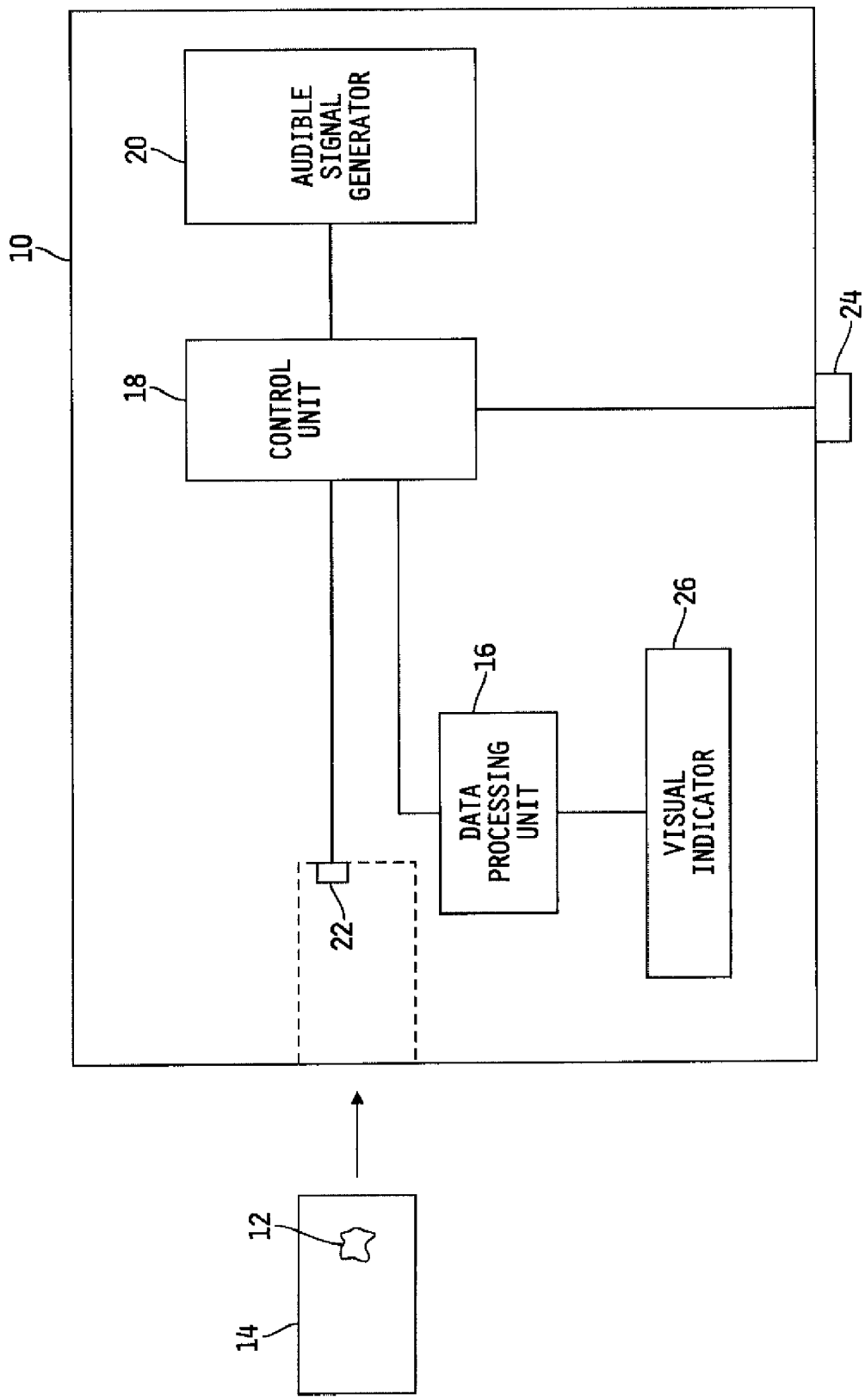
FIG. 1 is a block diagram representation of an analysis system for analyzing a fluid sample.

With reference to FIG. 1, an analysis system 10 is a system for analysing a fluid sample 12, for example for analysing blood, urine or interstitial fluid, particularly a blood sugar meter. The data processing unit 16 in the analysis system 10 receives the analysis results generated in the analysis of a fluid sample 12 arranged on the test element 14 and processes them. By way of example, it takes the analysis results measured (e.g. photometrically or electrochemically) and calculates the concentration of an analyte in the fluid sample 12. The control unit 18 contained in the analysis system 10 actuates the signal generator 20, inter alia, for example when the signal generator 20 is intended to be used to output the information about which analysis result processed by the data processing unit 16 has been obtained from the analysis of a fluid sample 12.

The audible signal generator 20 provided in the analysis system 10 may be any audible signal generator with which a person skilled in the art is familiar, e.g. a buzzer, a loudspeaker or a piezoelectric signal generator.

The information which is output may be a piece of information relating to the operating status of the analysis system 10 or to an analysis result, for example.

The signal generator 20 in the analysis system 10 sends an audible test signal in order to test the operability of the signal generator 20. The user of the analysis system 10 is then able to identify whether or not the audible test signal is correct. If the audible test signal is not sent correctly by the signal generator 20, it can be assumed that a piece of information which has been output by the audible signal generator 20 might likewise be incorrect.

The illustrated analysis system 10 contains a switch 22 which is tripped by a test element's being pushed or inserted into the analysis system 10, the switch 22 being coupled to the controller 18 such that the controller 18 actuates the signal generator 20 to send an audible test signal when the switch 22 is tripped. In this case, a test element 14 needs to be pushed or inserted into the analysis system 10 manually or automatically before a fluid sample 12 is analysed, into a sample holding position for holding the fluid sample 12 on the test element 14 and/or a measuring position for performing a measurement and generating analysis results.

However, the audible test signal may also be sent as soon as the user of the analysis system 10 pushes a particular button 24 on the analysis system 10 (e.g. the button for turning on the analysis system) or automatically at at least one particular instant during operation of the analysis system 10.

In one embodiment the signal generator 20 sends an audible test signal which comprises a tone or a sequence of tones, the tone or the sequence of tones essentially having a constant frequency or the tone or the sequence of tones having a changing frequency. The sequence of tones may be sent such that the individual tones merge into one another or are at least to some extent interrupted by pauses between the tones.

In addition, the signal generator 20 may send an audible test signal which comprises a sequence of tones, at least some of the tones having different tone lengths or the tones having essentially the same tone length.

The audible signal generator 20 may also send an audible test signal which comprises a tone or a sequence of tones, the volume of the tone or of the sequence of tones changing or the tone or the sequence of tones having essentially the same volume.

Particularly with regard to tone frequencies, tone lengths, tone volumes, and changes of frequencies and volume, the audible test signal should have as many of the features as possible which an audible signal sent by the signal generator 20 during normal operation of the analysis system 10 for the purpose of outputting a piece of information can have. If an audible signal of this kind for outputting a piece of information comprises merely a sequence of tones having essentially the same frequency, tone length and volume, with the individual tones being interrupted by pauses, then the test signal should have at least the same features to be able to detect a malfunction reliably. In addition, the test signal should be designed as far as possible such that a user can easily identify the correct test signal and any deviations therefrom.

In one embodiment the signal generator 20 sends the test signal at the start of the analysis system's being started up. Alternatively, the signal generator 20 can send the or at least one additional test signal at any other instant during operation of the analysis system 10. By sending the test signal at the start of the analysis system's being started up, the user can refrain from performing an analysis if he detects a malfunction in the audible signal generator 20 in the analysis system 10 right at the start. This means that it is possible to avoid, by way of example, taking useless painful blood samples or wasting test elements 14 for analyses using the analysis system 10 which are not able to be used on account of the malfunction in the audible signal generator 20. Alternatively, upon identifying an incorrect test signal, the user can ask a supervisor whose vision is not impaired to read off the information from a visual indicator if a visual indicator of this kind is available.

The sending of the test signal right at the start of the analysis system's being started up can be triggered by the analysis system's being turned on or by a test element's being pushed into the analysis system 10 automatically or by the user, for example. The operability of the signal generator 20 can be checked using the audible test signal at the same time as the operability of a visual indicator 26 in the analysis system 10, e.g. a liquid crystal display, is checked, which means that there is no need to accept any additional delay until the analysis system 10 is ready for use.

In one embodiment the audible signal generator 20 audibly encodes a piece of information which can be represented as a number with at least one digit. By way of example, the number may be a concentration (ascertained using the analysis system) for an analyte in a sample 12 analysed on a test element 14, particularly the glucose concentration in blood. The number may comprise one or more digits and may possibly have places after a decimal point.

In addition or as an alternative thereto, the piece of information encoded by the audible signal generator 20 may comprise a piece of information regarding the operational readiness of the analysis system 10 (e.g. the fact that the analysis system has been turned on) or a piece of information about the instant for a particular action to be performed by the user (e.g. the instant for applying his finger to a piercing aid integrated in the analysis system 10 or the instant for transferring a sample 12 for analysis to a test element 14). The signal generator 20 may also audibly output a piece of information regarding the need to replace or refill a consumable used in the analysis system 10 (e.g. test element, test element magazine, battery, lancet or disposable).

In one embodiment the audible signal generator 20 audibly encodes a piece of information as a sequence of tones, the number of tones denoting the piece of information. By way of example, a number can be audibly output such that a number of audible output tones respectively corresponds to a digit value for each digit in the number, with the output of a respective new digit being indicated by a longer pause or another audible signal, for example. In addition, a particular audible signal may be provided for a decimal point and/or an arithmetic sign.

The invention also relates to the use of an audible signal generator, which, for the purpose of audibly outputting a piece of information, is arranged in an analysis system for analysing a sample using a test element, for checking the operability of the signal generator by sending an audible test signal.

The invention claimed is:

1. A method of operating an audible signal generator in an analysis system configured to analyse a fluid sample arranged on a test element, the method comprising controlling the signal generator to generate an audible test signal, the audible test signal including audible features that allow for audible identification by a user of the analysis system of a correctly generated audible test signal and any deviations therefrom.

2. The method of claim 1 wherein controlling the signal generator comprises controlling the signal generator to generate the audible test signal only upon detection of start up of the analysis system.

3. The method of claim 2 further comprising detecting start up of the analysis system when the test element is inserted into the analysis system.

4. The method of claim 2 further comprising detecting start up of the analysis system when the analysis system is turned on.

5. The method of claim 1 wherein controlling the signal generator comprises controlling the signal generator to generate the audible test signal automatically at least one particular instant during operation of the analysis system.

6. The method claim 1 further comprising controlling the audible signal generator to include in the audible features at least one audible feature in the form of a number having at least one digit.

7. The method of claim 6 further comprising analysing the fluid sample to determine a concentration of an analyte contained in the fluid sample,
wherein the number corresponds to the concentration of the analyte in the fluid sample.

8. The method of claim 1 further comprising controlling the audible signal generator to include in the audible features at least one audible feature relating to the operational readiness of the analysis system.

9. The method of claim 1 further comprising controlling the audible signal generator to include in the audible features at least one audible feature relating to an instant for a particular action to be performed by a user of the analysis system.

10. The method of claim 1 further comprising controlling the audible signal generator to include in the audible features at least one audible feature relating to a need to replace or refill a consumable used in the operation of the analysis system.

11. The method of claim 1 further comprising controlling the audible signal generator to include in the audible features at least one audible in the form of a sequence of a number of tones, the number of tones in the sequence denoting information contained in the test signal.

12. The method of claim 1 wherein controlling the signal generator comprises controlling the signal generator to generate the audible test signal in the form of a tone or a sequence of tones, the tone or sequence of tones having a constant or changing frequency.

13. The method of claim 1 wherein controlling the signal generator comprises controlling the signal generator to generate the audible test signal in the form a sequence of tones, at least some of the tones in the sequence of tones having the same or different tone lengths.

14. The method of claim 1 wherein controlling the signal generator comprises controlling the signal generator to generate the audible test signal in the form of a tone or a sequence of tones, the tone or sequence of tones having constant or changing volume.

15. The method of claim 1 further comprising controlling the audible signal generator to include in the audible features at least one audible feature from which malfunction of the signal generator can be detected.

16. The method of claim 1 further comprising controlling the audible signal generator to include in the audible features at least one audible feature that tests the operability of the signal generator to encode information.

17. The method of claim 1 wherein the analysis system includes a switch positioned to be tripped by insertion of the test element into the analysis system,
and wherein the method further comprises controlling the audible signal generator to generate the audible test signal when the switch is tripped by insertion of the test element into the analysis system.

18. The method of claim 1 wherein the analysis system includes a user accessible button and wherein the analysis system turns on when the user accessible button is pressed,
and wherein the method further comprises controlling the audible signal generator to generate the audible test signal when the user accessible button is pressed.

* * * * *

UNITED STATES PATENT AND TRADEMARK OFFICE
CERTIFICATE OF CORRECTION

PATENT NO.         : 7,658,091 B2                                    Page 1 of 1
APPLICATION NO.  : 11/565149
DATED              : February 9, 2010
INVENTOR(S)        : Werner et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 275 days.

Signed and Sealed this

Thirtieth Day of November, 2010

David J. Kappos
*Director of the United States Patent and Trademark Office*